United States Patent
Lentz et al.

(10) Patent No.: US 9,085,097 B2
(45) Date of Patent: Jul. 21, 2015

(54) REINFORCED CATHETER OR SHEATH WITH REDUCED FRICTION SURFACE

(75) Inventors: David Christian Lentz, Bloomington, IN (US); David A. Drewes, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1004 days.

(21) Appl. No.: 12/714,589

(22) Filed: Mar. 1, 2010

(65) Prior Publication Data

US 2011/0213303 A1 Sep. 1, 2011

(51) Int. Cl.
| | |
|---|---|
| A61M 25/00 | (2006.01) |
| A61M 31/00 | (2006.01) |
| B29C 47/02 | (2006.01) |
| B29C 47/00 | (2006.01) |
| B29K 77/00 | (2006.01) |
| B29L 31/00 | (2006.01) |

(52) U.S. Cl.
CPC .............. B29C 47/02 (2013.01); A61M 25/005 (2013.01); A61M 25/0012 (2013.01); A61M 25/0045 (2013.01); B29C 47/0023 (2013.01); A61M 2025/006 (2013.01); A61M 2025/0062 (2013.01); B29C 47/0014 (2013.01); B29K 2077/00 (2013.01); B29L 2031/7542 (2013.01)

(58) Field of Classification Search
USPC ........................ 604/103.08–103.09, 172, 265, 604/523–524, 526–528, 366, 367, 370–311, 604/385.01, 385.31
See application file for complete search history.

(56) References Cited

U.S. PATENT DOCUMENTS

| | | | | |
|---|---|---|---|---|
| 2,998,397 | A * | 8/1961 | Riesing ............................ | 524/32 |
| 4,705,511 | A * | 11/1987 | Kocak ............................ | 604/524 |
| 4,925,710 | A * | 5/1990 | Buck et al. ..................... | 428/34.5 |
| 4,966,202 | A * | 10/1990 | Bryan et al. .................... | 138/172 |
| 5,201,314 | A | 4/1993 | Bosley et al. | |
| 5,248,472 | A * | 9/1993 | Yoshikawa et al. ........... | 264/519 |
| 5,289,831 | A | 3/1994 | Bosley | |
| 5,334,169 | A * | 8/1994 | Brown et al. .................. | 604/527 |
| 5,451,424 | A * | 9/1995 | Solomon et al. ............... | 427/2.1 |
| 5,531,721 | A * | 7/1996 | Pepin et al. .................... | 604/525 |
| 5,921,933 | A | 7/1999 | Sarkis et al. | |
| 6,086,970 | A * | 7/2000 | Ren ................................ | 428/36.9 |
| 6,197,015 | B1 * | 3/2001 | Wilson .......................... | 604/524 |
| 6,506,156 | B1 | 1/2003 | Jones et al. | |
| 6,610,016 | B1 | 8/2003 | Violante et al. | |
| 6,841,214 | B1 | 1/2005 | Keith et al. | |
| 7,014,610 | B2 | 3/2006 | Koulik | |
| 7,147,647 | B2 * | 12/2006 | Onyekaba et al. ............. | 606/152 |
| 2001/0027310 | A1 | 10/2001 | Parisi et al. | |
| 2004/0137160 | A1 * | 7/2004 | Ishihara et al. ................ | 427/428 |
| 2006/0204535 | A1 * | 9/2006 | Johnson ......................... | 424/422 |
| 2007/0202150 | A1 * | 8/2007 | Dave .............................. | 424/426 |

* cited by examiner

Primary Examiner — Quynh-Nhu H Vu
(74) Attorney, Agent, or Firm — Liell + McNeil

(57) ABSTRACT

A reinforced catheter or sheath includes an inner tube manufactured via an extrusion process from a mixture of thermoplastic and hollow glass beads. The resultant tube exhibits an inner goose bump surface that defines a central lumen. A reinforcement, such as a braid and/or coil is attached to at least a segment of the outer surface of the inner tube. A second tube of thermoplastic is extruded over at least a portion of the reinforcement. The inner goose bump surface exhibits a net low coefficient of friction comparable to that of polytetrafluoroethylene (PTFE).

20 Claims, 2 Drawing Sheets

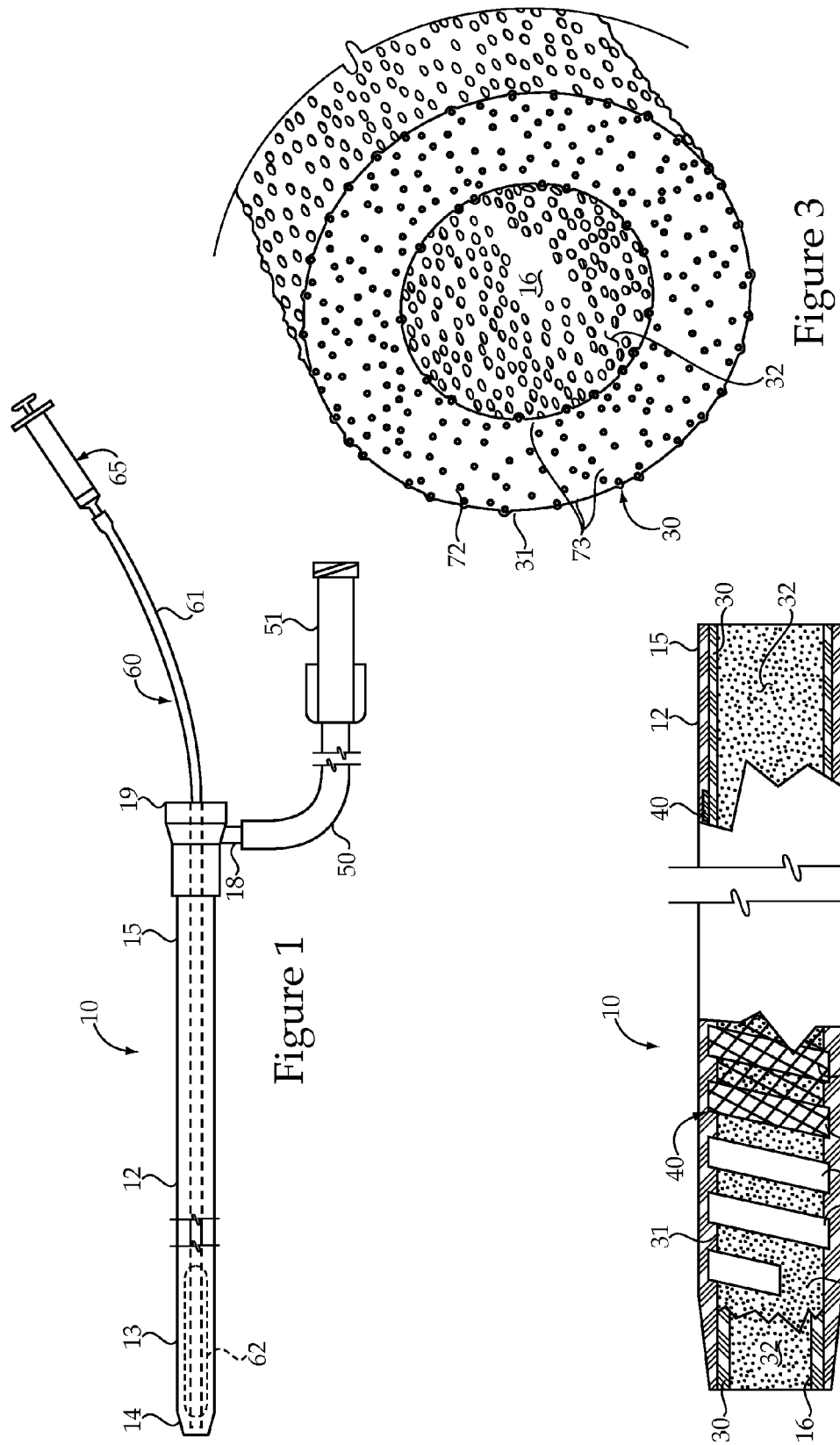

REINFORCED CATHETER OR SHEATH WITH REDUCED FRICTION SURFACE

TECHNICAL FIELD

The present disclosure relates generally to reinforced tubing for medical applications, and more particularly to a reinforced catheter or sheath formed via a continuous non-batch thermoplastic extrusion process.

BACKGROUND

Guide catheters and introducer sheaths are used in surgical applications to provide a passageway through which medical devices and/or therapeutic agents may be introduced within the body of a patient. In intravascular and coronary applications, such medical devices may include balloon dilation catheters, guide wires and other therapeutic devices, and the therapeutic agents typically include contrast media or other therapeutic fluids.

Guide catheters and introducer sheaths have a composite construction that includes a hollow shaft defined by an inner tube through which the medical devices or agents are delivered once the shaft has been inserted into the body of the patient. The inner tube typically comprises a lubricious material such as polytetrafluoroethylene (PTFE), commonly known as teflon. A reinforcement, such as a metal braid or coil surrounds the inner tube in order to provide kink resistance and torqueability, while retaining flexibility of the overall guide catheter or introducer sheath. An outer tube is typically formed from a polyether-block amide material marketed under the Trademark PEBAX or another equivalent material that is often applied via a shrink wrap process. Guide catheters and introducer sheaths are typically manufactured in a batch process utilizing precut lengths of PTFE tubing, as PTFE is known to be difficult to manage relative to standard thermoplastics in a continuous non-batch extrusion type process. The precut lengths of PTFE tubes are made kink resistant by applying a metal reinforcement, such as a coil or braid, around that fixed length of PTFE tubing. Next, an outer shrink wrap tube is slid over the sub-assembly. This assembly has been heated to activate the shrink tubing and mount the same onto the outer surface of the reinforcement and PTFE inner tube. The use of shrink tubing may add significant material costs to guide catheters and introducer sheaths. In addition, the labor and tooling required to manufacture guide catheters and introducer sheaths in a batch process can be significant.

A simple extrusion process for the inner tube using readily available thermoplastic materials, such as nylon, may appear at first glance to be a low cost alternative to the PTFE batch process currently used. However, thermoplastics tend to present a substantially higher co-efficient of friction than that associated with PTFE. Thus, common thermoplastics are generally not considered suitable for defining the inner lumen of guide catheters and introducer sheaths that must allow other devices to be easily slid through the inner lumen to remote locations within a patient being treated.

The present disclosure is directed toward one or more of the problems set forth above.

SUMMARY OF THE INVENTION

In one aspect, a catheter or sheath comprises a mixture, which includes thermoplastic and beads, defining a first tube with an inner goose bump surface and an outer surface. A reinforcement is attached to at least a segment of the outer surface. A second tube covers at least a portion of the reinforcement.

In another aspect, a method of making a reinforced catheter or sheath includes extruding a mixture of thermoplastic and beads into a first tube with an inner goose bump surface. A reinforcement is attached to at least a segment of an outer surface of the first tube. A second tube is then extruded over at least a portion of the reinforcement.

In still another aspect, a medical device assembly includes a reinforced catheter or sheath with a lumen defined by a goose bump surface, and a reinforcement position between the goose bump surface and an outer surface. A balloon catheter is slidably positioned in the lumen of the reinforced catheter or sheath.

DESCRIPTION OF THE DRAWINGS

FIG. 1 is a side elevational view of a medical device assembly according to one aspect of the present disclosure;

FIG. 2 is a sectioned view through the reinforced catheter or sheath of the medical device assembly shown in FIG. 1;

FIG. 3 is a sectioned perspective view of an inner tube for the reinforced catheter or sheath of FIG. 2.

DETAILED DESCRIPTION

Figure 4:
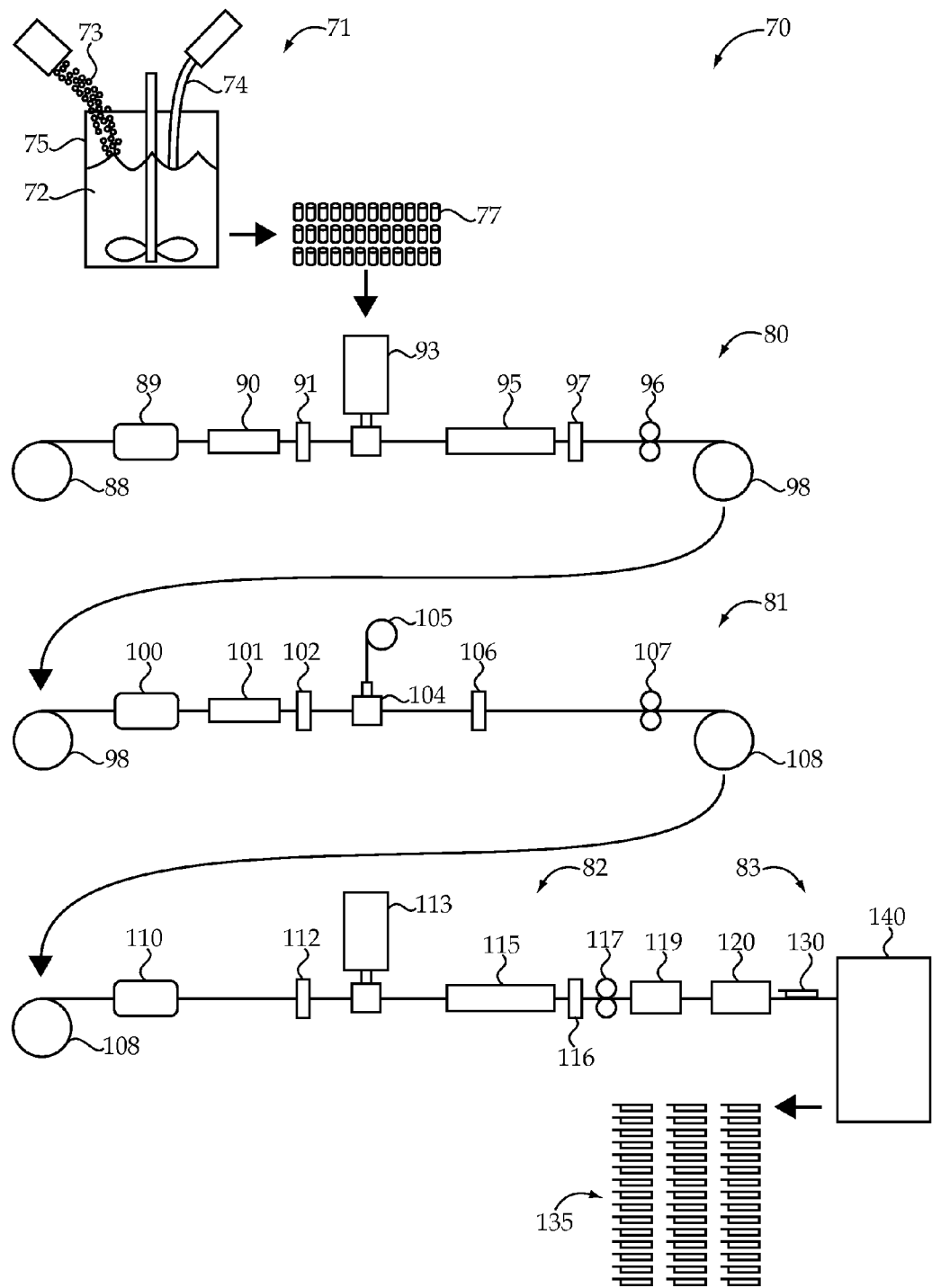
FIG. 4 is a schematic view of a manufacturing process for making the reinforced catheter or sheath of FIG. 2.

Referring to FIG. 1, a reinforced catheter or sheath 10 is commonly used in the medical arts for treatment at remote locations that are accessed through natural body passageways. In order to be functional, reinforced catheters and sheaths usually necessitate a low friction inner surface to accommodate the sliding interaction with other devices, such as wire guides, catheters or the like. In the example of FIG. 1, a medical device assembly 9 includes the reinforced catheter or sheath 10 that has slidably received a balloon catheter 60. Thus, the medical device assembly 9 shown in FIG. 1 might be appropriate for an angioplasty treatment of a location within a patient's circulatory system. Reinforced catheter or sheath 10 has a familiar structure in the inclusion of an outer tube 12 with a distal segment 13 that terminates in a tapered tip 14. A proximal segment 15 of reinforced catheter or sheath 10 terminates in a suitable fitting 19, which may include a side port 18. In the illustrated example, side port 18 is attached to a connecting tube 50 that terminates in a fitting 51. The balloon catheter 60 includes an inflation tube 61 that extends between an inflation syringe 65 and a balloon 62.

Referring now to FIG. 2, reinforced catheter or sheath 10 is shown partially sectioned to better illustrate its internal construction. In particular, reinforced catheter or sheath 10 includes an inner tube 30 with an inner goose bump surface 32 that defines a lumen 16 extending the length of the device. A reinforcement 40 is mounted on an outer surface 31 of the inner tube 30. Finally, an outer tube 12 covers reinforcement 40 and is bonded to inner tube 30 through gaps in reinforcement 40. Reinforcement 40 may comprise a coil or braid, and sometimes both, of the type known in the art to inhibit kinking and also to support torqueability of the reinforced catheter or sheath 10 in a conventional manner. According to the present disclosure, a goose bump surface is one that includes multiple randomly distributed rounded protuberances rising out of an otherwise smooth base surface. Inner tube 30 is preferably comprised of a mix containing thermoplastic and microscopic beads of a suitable material. As used in the context of this disclosure, a thermoplastic is a polymer that turns to a liquid when heated and freezes to a glassy state when cooled, such that the material is particularly suited to extrusion molding techniques. Thus, for instance, polymides such as nylon and elastomers such as polyester block amide would be considered thermoplastics according to the present disclosure, but PTFE would not. Beads according to the present disclosure may be of any suitable material including but not limited to solid or hollow glass beads.

In one specific example, hollow glass spheres with diameters of about eighteen microns plus/minus one micron are embedded in nylon and occupy about 17% of the volume of inner tube 30. Nevertheless, those skilled in the art would appreciate that any suitable combination of size or sizes in various proportions with the surrounding thermoplastic would fall within the intended scope of the present disclosure. Hollow glass spheres may be particularly attractive for their ecogenetic properties over and above the ability to produce the low friction goose bump inner surface that defines lumen 16. Although thermoplastic is not generally known for its low coefficient of friction, it is believed that the goose bump surface 32 provides such a dramatic reduction in contact area between the reinforced catheter or sheath 10 and another medical device slid therethrough, such as balloon catheter 60, that the goose bump surface 32 produces apparent low friction results comparable to PTFE. Although not necessary, in addition to hollow glass beads and thermoplastic, inner tube 30 may also include a conventional radiopaque additive in a percentage sufficiently high to facilitate fluoroscopic imaging during patient treatment.

A close up cross sectional view of inner tube 30 is shown in FIG. 3. This view shows a relatively random distribution of hollow glass microspheres 73 (beads) embedded in a thermoplastic (e.g. nylon) matrix such that each glass sphere is encased in thermoplastic, rather than presenting an exposed glass surface. For reasons not completely understood, conventional extrusion processes using a mixture of thermoplastic 72 with embedded glass beads 73 produces the goose bump surface features 32 on the inner and outer surfaces of extruded tube 30. No special extruding techniques are necessary in order to accomplish the goose bump texturing. However, extrusion processes altered to better facilitate the production of goose bump surface features would also fall within the intended scope of the present disclosure.

Referring now to FIG. 4, a manufacturing process 70 is illustrated as one method for making reinforced catheters or sheaths 10 according to the present disclosure. Manufacturing process 70 may include a mixing process 71, a first extrusion process 80, a reinforcing process 81, a second extrusion process 82 and a finishing process 83. Mixing process 71 involves an ordinary mixer 75 for mixing thermoplastic 72 with beads 73, and maybe with the addition of a radiopaque additive 74. The output of the mixing process 71 may include forming the mixture into a plurality of pellets 77 that may be suitable for transport and/or storage in a conventional manner prior to being heated and molded.

The first extrusion process 80 involves unrolling a mandrel spool 88, coating the mandrel with extruded material from melted pellets 77 and then gathering the resultant mandrel and tube extrusion on an inner tube spool 98. In particular, mandrel 88 may comprise any suitable material such as a smooth rod that is advanced through a heater 89, through a lubricant applicator 90 and past a measurer 91 to extruder 93. Extruder 93 deposits a substantially uniform wall thickness inner tube 30 (FIG. 3), onto the acytyl rod mandrel. After extruder 93, the extruded material and mandrel are passed through a cooler 95, through another measurer 97, past a puller 96 and onto inner tube spool 98. Thus, an extended length of inner tube product can be made using conventional extrusion techniques in a continuous process.

The resultant combination inner tube and mandrel spool 98 is the beginning portion of the reinforcing process 81. Nevertheless, those skilled in the art will appreciate that no intervening spooling may be necessary if processes 80, 81 and 82 were all arranged in series. The inner tube spool 98 is unrolled and the strand may pass through a heater 100, maybe an adhesive applicator 101 and a measurer 102 before arriving at an applicator 104. Applicator 104 applies a coil or braid reinforcement in a known manner, which may be drawn continuously off of a reinforcer spool(s) 105 in the illustrated example. A second applicator (not shown) may be included in those cases where both a coil and braid are to be applied. After passing through applicator 104, another measurer 106 may confirm the diameter of the reinforced strand before puller 107 recollects the partially manufactured reinforced tube spool 108, which forms the beginning of the second extrusion process 82.

The reinforced strand of reinforced tube is drawn from spool 108, through a heater 110, past a measurer 112 and through a second extruder 113. Extruder 113 preferably uses a thermoplastic of a type that easily bonds, and maybe even blends, with the thermoplastic 72. In fact, the same pellets 77 that include mixture of beads 73 and radiopaque additive 74 may also be used for extruding the outer tube from extruder 113. After passing through extruder 113, the strand is cooled in cooler 115 and passes through a final measurer 116 before being pulled via puller 117. Next, a finisher 119 is utilized to cut fixed lengths of the material, remove the inner mandrel, shape a taper on distal end of the cut segment and possibly attach a fitting to a proximal end of the cut segment to produce a finished reinforced catheter or sheath 10 of the type illustrated in FIG. 1. Next, the individual reinforced catheters or sheaths may be passed through a packager 120 and individually deposited into packages 130, such as peel away plastic containers. Finally, the packages are passed through a sterilizer 140 with the resultant product being a plurality of peel away packages 135 each including an individual finished sterile reinforced catheter or sheath 10 of the type shown in FIG. 1.

INDUSTRIAL APPLICABILITY

The present disclosure is generally applicable to reinforced tubing manufactured from thermoplastic. The present disclosure finds particular application in the manufacture of reinforced catheters or sheaths of the type used in a variety of medical treatments that require a relatively low coefficient friction inner surface to facilitate the sliding of other medical devices, such as wire guides, balloon catheters and the like. The present disclosure finds specific applicability to replacing the relatively time consuming and expensive batch production strategy typically associated with reinforced catheters or sheaths that utilize a low friction PTFE inner tube in their construction. The present disclosure is especially applicable to replacing such batch processes with a low cost multi step extrusion process using conventional thermoplastics combined with microscopic beads, such as hollow glass spheres, and may also include a radiopaque additive to render the device visible under ultrasound and/or fluoroscopy.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A reinforced catheter or sheath comprising:
a mixture, which includes thermoplastic and beads, defining a first tube with an inner goose bump surface defined by the thermoplastic and an outer surface, and the inner goose bump surface includes randomly distributed rounded protuberances rising out of a smooth base surface, and the beads are encased in the thermoplastic;
a reinforcement attached to at least a segment of the outer surface;
a second tube covering at least a portion of the reinforcement; and
wherein the inner goose bump surface reduces a contact area between the thermoplastic of the first tube and another medical device slid therethrough to produce an apparent low friction.

2. The catheter or sheath of claim 1 wherein the beads include glass beads.

3. The catheter or sheath of claim 2 wherein the glass beads are hollow glass beads.

4. The catheter or sheath of claim 1 wherein the reinforcement includes a braid.

5. The catheter or sheath of claim 1 wherein the reinforcement includes a coil.

6. The catheter or sheath of claim 1 wherein the thermoplastic includes nylon.

7. The catheter or sheath of claim 1 wherein the second tube is defined by thermoplastic that is blended with the thermoplastic of the first tube.

8. The catheter or sheath of claim 1 wherein the mixture includes a radiopaque additive.

9. The catheter or sheath of claim 3 wherein the reinforcement includes a braid.

10. The catheter or sheath of claim 3 wherein the reinforcement includes a coil.

11. The catheter or sheath of claim 3 wherein the thermoplastic includes nylon.

12. The catheter or sheath of claim 3 wherein the second tube is defined by thermoplastic that is blended with the thermoplastic of the first tube.

13. The catheter or sheath of claim 3 wherein the mixture includes a radiopaque additive.

14. A method of making a reinforced catheter or sheath, comprising the steps of:
extruding a mixture of thermoplastic and beads into a first tube with an inner goose bump surface defined by the thermoplastic, and the inner goose bump surface includes randomly distributed rounded protuberances rising out of a smooth base surface, and the beads are encased in the thermoplastic;
attaching a reinforcement to at least a segment of an outer surface of the first tube; and
extruding a second tube over at least a portion of the reinforcement; and
wherein the inner goose bump surface reduces a contact area between the thermoplastic of the first tube and another medical device slid therethrough to produce an apparent low friction.

15. The method of claim 14 wherein the step of attaching a reinforcement includes mounting at least one of a coil and a braid onto the outer surface.

16. The method of claim 14 including mixing thermoplastic, glass beads and a radiopaque additive into the mixture.

17. The method of claim 16 wherein the step of extruding a second tube includes blending a thermoplastic of the second tube with the thermoplastic of the first tube at the outer surface.

18. The method of claim 14 wherein the step of extruding a second tube includes extruding a mixture of thermoplastic and beads over at least a portion of the reinforcement.

19. A medical device assembly comprising:
a reinforced catheter or sheath with a lumen defined by a goose bump surface of thermoplastic, and including a reinforcement positioned between the goose bump surface and an outer surfaces, and the goose bump surface includes randomly distributed rounded protuberances rising out of a smooth base surface; and
a balloon catheter slidably positioned in the lumen of the reinforced catheter or sheath;
wherein the inner goose bump surface reduces a contact area between the thermoplastic of the reinforced catheter and balloon catheter slid therethrough to produce an apparent low friction.

20. The reinforced catheter or sheath of claim 1 wherein the beads occupy 17% by volume of the inner tube;
the beads are hollow glass spheres with an average diameter of 18 microns; and
the thermoplastic is nylon.

* * * * *